(12) United States Patent
Biederman et al.

(10) Patent No.: US 10,512,723 B1
(45) Date of Patent: *Dec. 24, 2019

(54) CONTROL OF A PERIPHERAL DEVICE WITH A BANDAGE-TYPE ANALYTE SENSOR

(71) Applicant: Verily Life Sciences LLC, Mountain View, CA (US)

(72) Inventors: William James Biederman, Fox Island, WA (US); Brian Otis, Saratoga, CA (US); Jaclyn Leverett Wasson, Berkeley, CA (US); Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 16/034,633

(22) Filed: Jul. 13, 2018

Related U.S. Application Data

(63) Continuation of application No. 14/719,980, filed on May 22, 2015, now Pat. No. 10,046,114.

(51) Int. Cl.
*A61M 5/172* (2006.01)
*A61B 5/00* (2006.01)
*A61B 5/1473* (2006.01)
*A61B 5/145* (2006.01)

(52) U.S. Cl.
CPC ......... *A61M 5/1723* (2013.01); *A61B 5/0024* (2013.01); *A61B 5/1451* (2013.01); *A61B 5/1473* (2013.01); *A61B 5/14532* (2013.01)

(58) Field of Classification Search
CPC .. A61M 5/1723; A61B 5/0024; A61B 5/1451; A61B 5/14532; A61B 5/1473
See application file for complete search history.

(56) References Cited

U.S. PATENT DOCUMENTS

| | | | |
|---|---|---|---|
| 3,958,560 A | 5/1976 | March | |
| 7,949,382 B2 | 5/2011 | Jina | |
| 8,280,476 B2 | 10/2012 | Jina | |
| 2007/0112261 A1 | 5/2007 | Enegren et al. | |
| 2011/0208155 A1* | 8/2011 | Palerm | G06F 19/3456 604/503 |
| 2012/0163481 A1* | 6/2012 | Ebner | A61B 5/0002 375/259 |

(Continued)

OTHER PUBLICATIONS

Dexcom G4 Platform, Continuous Glucose Monitoring System, Quick Start Guide, Dexcom, Inc. copyright 2013, 2 pages.

(Continued)

*Primary Examiner* — Lauren P Farrar
(74) *Attorney, Agent, or Firm* — McDonnell Boehnen Hulbert & Berghoff LLP

(57) ABSTRACT

An example system includes a flexible substrate configured to be mounted to a skin surface. The system includes a sensor probe that has a first end attached to the flexible substrate and a second end configured to extend beneath the skin surface to contact interstitial fluid. A sensor is configured to measure a physiological property and is disposed at the second end of the sensor probe. A transmitter is attached to the flexible substrate and is configured to provide information related to sensor measurements to a controller. The controller is configured to a drug delivery rate based on the information.

20 Claims, 6 Drawing Sheets

(56) References Cited

U.S. PATENT DOCUMENTS

2012/0245444 A1    9/2012   Otis et al.
2014/0247148 A1*   9/2014   Proud .................... H02J 7/025
                                                                                        340/870.02

OTHER PUBLICATIONS

Dexcom G4 Platform Professional, Professional Continuous Glucose Monitoring System, Users Guide, Dexcom, Inc. copyright 2014, 258 pages.
Medtronic with Guardian Real-Time Continuous Glucose Monitoring-Getting Started, Medtronic MiniMed, Inc., copyright 2009, 28 pages.
Medtronic Guardian Real-Time Continuous Glucose Monitoring System-User Guide, Medtronic MiniMed, Inc., copyright 2006, 184 pages.
Non-Final Office Action issued in Co-pending U.S. Appl. No. 14/088,280 dated Aug. 19, 2015, U.S. Patent and Trademark Office, 12 pages.

* cited by examiner

CONTROL OF A PERIPHERAL DEVICE WITH A BANDAGE-TYPE ANALYTE SENSOR

CROSS REFERENCE TO RELATED APPLICATION

The present application is a continuation of U.S. patent application Ser. No. 14/719,980, filed on May 22, 2015, the entire contents of which are herein incorporated by reference as if fully set forth in this description.

BACKGROUND

Unless otherwise indicated herein, the materials described in this section are not prior art to the claims in this application and are not admitted to be prior art by inclusion in this section.

Certain medical conditions or states can be characterized by slow changes of a physiological property over long periods of time and/or by infrequent, short-timescale events. Such physiological properties can be measured periodically (e.g., by periodically accessing blood of a person). Additionally or alternatively, an implanted or wearable device could be employed to provide continuous or near-continuous measurement of such physiological properties. Such implantable or wearable devices can be battery powered.

SUMMARY

The present disclosure describes embodiments that relate to control of a peripheral device with a bandage-type analyte sensor. In one aspect, the present disclosure describes a system. The system includes a flexible substrate configured to be mounted to a skin surface. The system also includes a sensor probe having a first end attached to the flexible substrate and a second end configured to extend beneath the skin surface to contact interstitial fluid. The system further includes a sensor configured to measure a physiological property. The sensor is disposed at the second end of the sensor probe, and the physiological property is related to glucose in the interstitial fluid. The system also includes a near field communication (NFC) transmitter attached to the flexible substrate and configured to receive from the sensor one or more sensor measurements indicative of the physiological property. The system further includes a controller configured to: (i) receive information related to the one or more sensor measurements from the NFC transmitter while the controller is within a predetermined threshold distance from the NFC transmitter, (ii) determine a glucose concentration based on the information, (iii) obtain a target glucose concentration, (iv) compare the glucose concentration to the target glucose concentration, and (v) based on the comparing, provide instructions to an insulin delivery device to control an insulin delivery rate to a blood stream by the insulin delivery device.

In another aspect, the present disclosure describes a method. The method includes receiving, at a controller from an NFC transmitter, information indicative of one or more sensor measurements of a physiological property related to glucose in an interstitial fluid. The NFC transmitter is attached to a flexible substrate mounted to a skin surface. The one or more sensor measurements are captured by a sensor disposed at a first end of a sensor probe, the first end being configured to extend beneath the skin surface to contact the interstitial fluid, and the sensor probe having a second end attached to the flexible substrate. The method also includes determining a glucose concentration based on the information. The method further includes obtaining a target glucose concentration, and comparing the glucose concentration to the target glucose concentration. The method also includes, based on the comparing, providing instructions to an insulin delivery device to control an insulin delivery rate to a blood stream by the insulin delivery device.

In still another aspect, the present disclosure describes a non-transitory computer readable medium having stored thereon instructions that, when executed by a controller, cause the controller to perform operations. The operations comprise receiving, from an NFC transmitter, information indicative of one or more sensor measurements of a physiological property related to glucose in an interstitial fluid. The NFC transmitter is attached to a flexible substrate mounted to a skin surface. Further, the one or more sensor measurements are captured by a sensor disposed at a first end of a sensor probe, the first end being configured to extend beneath the skin surface to contact the interstitial fluid, and the sensor probe having a second end attached to the flexible substrate. The operations also include determining a glucose concentration based on the information. The operations further include obtaining a target glucose concentration, and comparing the glucose concentration to the target glucose concentration. The operations also include, based on the comparing, controlling an insulin delivery device to adjust an insulin delivery rate to a blood stream by the insulin delivery device.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION

Figure 1A:
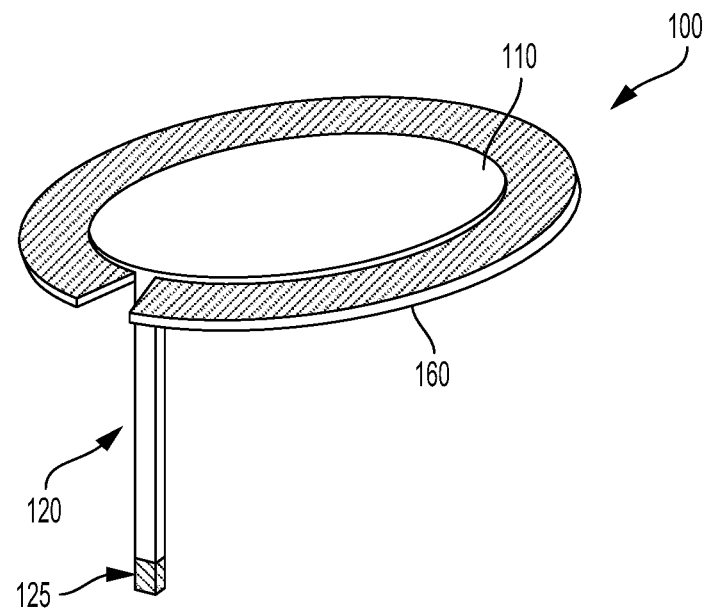
FIG. 1A is a top aspect view of an example body-mountable device, in accordance with an example implementation.

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

I. OVERVIEW

Some implementations of the present disclosure provide a body-mountable device configured to be mounted to a skin surface of a living body (e.g., to skin of an arm or abdomen of a person). The body-mountable device includes one or more sensors for quantitatively and qualitatively detecting one or more physiological properties (e.g., a heart rate, a temperature, a concentration of glucose or some other analyte in interstitial fluid or some other fluid) of the living body in real-time.

Elements of the body-mountable device are disposed on a flexible substrate that is configured to be mounted to the skin surface (e.g., by use of glue, tape, dry adhesive, or other adhesive means). The flexibility of the flexible substrate (and of the body-mountable device as a whole) could provide a sensing platform that minimally interferes with activities of a body to which the sensing platform is mounted and/or that can be mounted to a body comfortably for protracted periods of time. This could include the flexible substrate and/or the sensing platform being sufficiently flexible that the flexible substrate complies with the shape of the skin surface and deforms with changes in the shape of the skin surface. The sensing platform described herein may be provided in devices that could be mounted on a variety of portions of the human body to measure a variety of physiological properties of the human body (e.g., concentrations of a variety of analytes in a variety of fluids of the body, temperature, galvanic properties, ECG; muscle activity).

The sensing platform could include a variety of sensors configured to detect a variety of physiological properties and/or properties of the environment of the sensing platform. In some examples, the sensor could include an analyte sensor configured to detect an analyte (e.g., glucose) in a fluid on or within the skin surface to which the sensing platform is mounted (e.g., interstitial fluid within or beneath the skin).

The sensor could be disposed on a sensor probe that is configured to penetrate the skin (e.g., to a specified depth within the skin) such that the sensor can measure an analyte in a fluid within the skin. Such a sensor probe could be configured to penetrate to a specified depth within the skin (e.g., to a depth within the dermis, to a subcutaneous depth) such that at least one sensor disposed on the sensor probe can measure an analyte in fluid (e.g., interstitial fluid) at the specified depth.

A transmitter may be attached to the flexible substrate. The transmitter may be in communication with the sensor attached to the flexible substrate and may be configured to receive sensor measurements indicative of the physiological property. Further, the transmitter may be configured to provide signals indicative of the sensor measurements to a controller. For instance, the transmitter may be an NFC transmitter that, when the controller is within a threshold distance from the NFC transmitter, provides the signals to the controller. In another example, two transmitters may be attached to the flexible substrate. For instance, an NFC transmitter and a Bluetooth low energy (BLE) transmitter may be attached to the substrate. The two transmitters may be configured to provide different information to the controller. As an example, the NFC transmitter may provide data encryption information, initialize the sensor, transfer sensor calibration information, etc., whereas the BLE transmitter may provide the sensor data or measurements to the controller.

The controller may be configured to receive the signals from the NFC transmitter and determine physical properties based on the signals. For example, the controller may determine glucose concentration in a blood stream based on the signals indicative of glucose sensor measurements. In this example, the controller may further have access to a target glucose concentration, and may compare the glucose concentration to the target glucose concentration. Based on such comparison, the controller may control an insulin delivery device to control an insulin delivery rate to the blood stream by the insulin delivery device to maintain glucose concentration within a predetermined range about the target glucose concentration.

In examples, the controller could be separate or remote from the body-mountable device. The controller may be, for example, a wearable, laptop, desktop, handheld, or tablet computer, a mobile phone, or a subsystem of such a device. In other examples, the controller may be embedded in a device such as the insulin delivery device mentioned above. The controller may be in communication with a display device. The controller may be configured to provide glucose concentration information to the display device and generate a display of the information on the display device.

The examples mentioned above and throughout the disclosure are described in the context of measuring glucose concentration and controlling an insulin delivery device accordingly. However, the methods and systems described herein can be used for controlling levels of any other analyte by controlling any drug delivery device. An example controller may be configured to receive information or sensor measurements indicative of concentration of an analyte from a transmitter attached to a body-mountable device. The controller may then compare concentration of the analyte to a target analyte concentration. Based on the comparing, the controller may be configured to control a drug delivery device, where the instructions are configured to control a drug delivery rate by the drug delivery device so as to cause the concentration of the analyte to substantially meet the target analyte concentration.

II. EXAMPLE FLEXIBLE BIOSENSOR PLATFORM

Figure 1B:
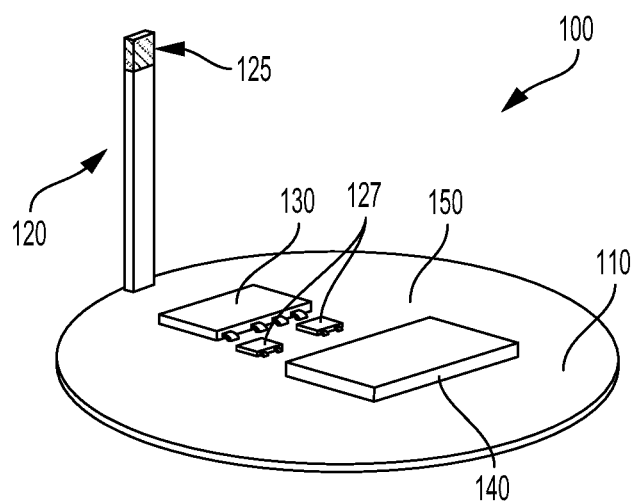
FIG. 1B is a bottom aspect view of the example body-mountable device shown in FIG. 1A, in accordance with an example implementation.

FIG. 1A is a top view of an example body-mountable sensing platform 100, in accordance with an example implementation. FIG. 1B is a bottom view of the example body-mountable sensing platform shown in FIG. 1A, in accordance with an example implementation. Relative dimensions in FIGS. 1A and 1B are not necessarily to scale, but have been rendered for purposes of explanation only in describing the arrangement of the example body-mountable sensing platform 100. The body-mountable device 100 is formed of a flexible substrate 110 shaped (as an illustrative example) as a circular disk.

A sensor probe 120 extends from the flexible substrate 110 and is configured to penetrate a skin surface (e.g., to penetrate into skin of an arm or abdomen of a human body). An analyte sensor 125 is disposed at a distal end of the sensor probe 120. The analyte sensor 125 is configured to detect an analyte (e.g., glucose) in interstitial or other fluids under and/or within the skin when the sensor probe 120 penetrates the skin. An optical sensor 127 is also included to optically detect one or more properties of skin (e.g., by illuminating and/or detecting light emitted from the skin to detect an optical property, e.g., a color, reflectivity, or other properties). An adhesive layer 160 is provided to mount the flexible substrate 110 to a skin surface (the adhesive layer 160 is not shown in FIG. 1B, to allow illustration of elements of the body-mountable sensing platform 100 that are disposed on the bottom surface 150 of the flexible substrate 110).

The body-mountable sensing platform 100 additionally includes electronics 130 disposed on the flexible substrate 110 and configured to perform various operations for the sensing platform 100. The operations include, for example, operating the analyte sensor 125 to detect an analyte, operating the optical sensor 127 to detect and optical property of skin, operating some other sensor of the sensing platform 100 to detect some other property or variable, recording information (e.g., measured concentrations of the analyte) in a memory of the electronics 130, and communicating information (e.g., by using an antenna to wirelessly indicate such information) to an external system. For example, the sensing platform 100 could include an NFC transmitter attached to the flexible substrate 110. The NFC transmitter may include an antenna (not shown) that could be configured as a loop antenna on bottom surface 150 (e.g., encircling electronics 130), or the antenna could be configured as a chip antenna or some other configuration. In another example, the sensing platform 100 may include more than one type of transmitters such as an NFC transmitter and a BLE transmitter providing different types of data.

A battery 140 is provided to power the body-mountable sensing platform 100 (e.g., to power the electronics 130). Components (e.g., antennas, batteries, electronics, etc.) could additionally or alternatively be disposed on the top surface of the flexible substrate 110 (i.e., the surface of the flexible substrate 110 opposite the bottom surface 150).

The flexible substrate 110 is configured to be mounted like a bandage to a skin surface. In the example shown in FIGS. 1A and 1B, this includes a layer of the adhesive 160 being provided to adhere the flexible substrate 110 to a skin surface. Additional or alternative means could be provided to mount the flexible substrate 110 to a skin surface. For example, a liquid or gel adhesive could be applied to the skin surface and/or to the flexible substrate 110 to mount the flexible substrate 110 to the skin surface. The flexible substrate 110 could be placed on the skin surface and secured using tape or other adhesives. In some examples, the body-mountable sensing platform 100 could include a dry adhesive configured to removably mount the flexible substrate 110 to a skin surface. Other means for mounting the flexible substrate 110 or other elements of the body-mountable sensing platform 100 to a skin surface or to other elements or aspects of a living body are anticipated. Further, in some implementations, the body-mountable sensing platform 100 could be placed proximate a target fluid (e.g., interstitial fluid, synovial fluid, blood, tears, saliva, mucus) without mounting to a skin surface or other tissue surface. For example, the body-mountable sensing platform 100 could be configured to be placed between the teeth and cheek of a living body, on the eye of a living body, or at some other location of a living body without being mounted to a particular tissue surface.

The flexible substrate 110 and/or elements of the body-mountable sensing platform 100 disposed thereon can have a thickness, shape, composition, rigidity, compliance, elasticity, viscoelasticity, and/or other properties specified such that the flexible substrate 110 can be mounted to a skin surface of a living body and further such that the mounting minimally interferes with activities of the living body (e.g., motions of the living body). This could include the flexible substrate 110 being sufficiently flexible that mounting the flexible substrate 110 to the skin surface causes a minimum of discomfort. The body-mountable sensing platform 100 could be sufficiently flexible that the flexible substrate 110 and components mounted thereto comply with the shape of the skin surface and deform with changes in the shape of the skin surface. For example, the components (e.g., electronic components, transmitter, sensors) could include or be composed of flexible polymers, flexible metal films, traces, and/or electrodes, or other flexible materials and/or materials formed to be flexible (e.g., a rigid material formed to include a strain relief, to be thin or narrow, or otherwise formed such that an element composed of the rigid material is functionally flexible).

Additionally or alternatively, rigid components (e.g., rigid electronic components) could be mounted to the flexible substrate 110 such that the body-mountable sensing platform 100 is, overall, flexible. For example, the rigid components could be small, or separated by a specified distance on the flexible substrate 110, or have a long shape and being disposed parallel to each other on the flexible substrate 110. This way, the body-mountable sensing platform 100 could be flexible in a direction perpendicular to the orientation of the rigid components. Being flexible indicates that the body-mountable sensing platform 100 is compliant and deforms according to deformations of the skin surface to which that body-mountable sensing platform 100 is mounted. In this manner, the body-mountable sensing platform 100 minimally interferes with activities of a body/ causes minimal discomfort.

The flexible substrate 110 could be composed of polyimide or some other flexible polymeric or other material. As an example, the flexible substrate 110 could have a thickness less than approximately 100 microns. Further, the flexible substrate 110 could have a size specified to minimally interfere with activities of the living body. For example, the flexible substrate 110 could have a size (e.g., a diameter of a circular portion, as illustrated in FIGS. 1A and 1B) less than approximately 11 millimeters. Diameter and thickness values are provided for explanatory purposes only. Further, the shape of the flexible substrate 110 could be different from that illustrated in FIGS. 1A and 1B or elsewhere herein. For example, the flexible substrate 110 could have an elongate shape, a square or rectangular shape, or some other shape according to an application. For example, the flexible substrate 110 could have an elongate shape to provide sufficient area for disposition of electronics, batteries, antennas, or other components on the flexible substrate 110. Such elongate shape construction may minimally impede motion and/or deformation of the skin surface to which the flexible substrate 110 is mounted.

One or more surfaces of the flexible substrate 110 (e.g., the bottom surface 150) could be used as a platform for mounting electronics such as chips (e.g., via flip-chip mounting). These surfaces could also be used for patterning conductive materials (e.g., via deposition techniques) to form electrodes, antenna(e), and/or connections. The composition of the flexible substrate 110 could be chosen to allow for the formation and/or disposition of such elements of the body-mountable sensing platform 100. For example, the flexible substrate 110 could be composed of polyimide or some other polymeric and/or metallic material(s) such that metal contacts, traces, and interconnects can be patterned directly on the surface of the flexible substrate 110. Example patterning techniques include sputtering, Chemical Vapor Deposition, or some other deposition process). The metal contacts, traces, and interconnects could also be patterned on a coating or layer formed on the one or more surfaces of the flexible substrate 110.

Further, such patterned structures and/or other elements disposed on the flexible substrate 110 (e.g., electronics 130, optical sensor 127, battery 140, antennas) could, in combination with the flexible substrate 110, have a thickness or other property specified to provide the overall body-mountable sensing platform 100 with flexibility. For example, the flexible substrate 110 in combination with electronics 130, optical sensor 127, and battery 140 disposed thereon could have a thickness less than approximately 0.5 millimeters.

One or more components of a sensor or other elements of the body-mountable sensing platform 100 could be formed directly on the flexible substrate 110 as a deposited metal film, dielectric material or coating, or other deposited material. Electrodes or other elements of an electrochemical analyte sensor, a galvanic skin resistance or potential sensor, an electromyogram (EMG) or electrocardiogram (ECG) sensor, or some other components could be formed by depositing metals or other materials on the flexible substrate 110. Additionally or alternatively, such elements could be formed separately from the flexible substrate 110 and deposited and/or disposed on the flexible substrate 110. Depositing and/or disposing the elements on the flexible substrate 110 can be performed using techniques involving an adhesive, welding, reflow soldering between contacts of the elements and corresponding metallic pads or traces formed on the flexible substrate 110.

The electronics 130 disposed on the flexible substrate 110 could include a variety of devices. For example, the electronics 130 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 110. Further, antennas, electrodes, capacitors, resistors, or other components could be formed from such traces or other interconnects formed on the surface of the flexible substrate 110.

The electronics 130 can include logic elements configured to operate the analyte sensor 125 to detect an analyte and the optical sensor 127 to detect an optical property of skin. The logic elements may further be configured to operate an antenna to wirelessly indicate information (e.g., concentration levels about a detected analyte). The antenna could be, for example, a loop, dipole, other type of antenna formed on the flexible substrate 110, or a chip antenna disposed on the flexible substrate 110. A loop, dipole, or other type of antenna can be one or more layers of conductive material patterned on the surface 150 of the flexible substrate 110 to form one or more specified conductive shapes. Example conductive shapes include a ring, a spiral, a curved or straight line, an elliptical or rectangular patch, a fractal, etc.

Electrical interconnects (e.g., traces), antennas, and/or conductive electrodes can be formed from conductive materials patterned on the flexible substrate 110 by a process for precisely patterning such materials, such as deposition, lithography, etc. The conductive materials patterned on the flexible substrate 110 can be, for example, gold, platinum, palladium, titanium, carbon, aluminum, copper, silver, silver-chloride, conductors formed from noble materials, metals, combinations thereof, etc.

The sensor probe 120 is an elongate element of the body-mountable sensing platform 100 that is configured to penetrate a skin surface. In this manner, the analyte sensor 125 located at the distal end of the sensor probe 120 contacts a fluid (e.g., interstitial fluid, blood) containing an analyte of interest (e.g., glucose) when the sensor probe 120 is penetrating the skin. For example, the sensor probe 120 could be more than approximately 2 millimeters long. The sensor probe 120 could have a length that enables the sensor 125 to contact tissue at a specified depth within the skin (e.g., tissue of the dermis of the skin, subcutaneous tissue). For example, the sensor probe 120 could have a length between approximately 500 microns and approximately 6000 microns. Further, the sensor probe 120 could have one or more dimensions specified to provide sufficient area for electrodes or other elements disposed on the sensor probe 120, to minimally interfere with the skin. For instance, the sensor probe 120 might require a minimal incision or other alteration of the skin to provide for penetration of the sensor probe 120. For example, the sensor probe 120 could have a width between approximately 25 microns and approximately 400 microns.

The sensor probe 120 could be composed of a variety of materials and elements formed by a variety of processes. The sensor probe 120 could be composed of a flexible material (e.g., polyimide) or a relatively inflexible material. Further, a thickness, width, shape, or other properties of the sensor probe 120 could be specified to provide a degree of flexibility or inflexibility. For example, a flexible sensor probe 120 could have a width between approximately 25 microns and approximately 400 microns and/or a thickness less than approximately 100 microns. In some examples, the sensor probe 120 could be formed from the same material as the flexible substrate 110.

In an example, the sensor probe 120 could be an elongate portion of the flexible substrate 110 that extends from a portion of the flexible substrate 110 that is configured to be mounted to a skin surface and/or on which electronics 130 or other components are disposed. Alternatively, the sensor probe 120 could be attached to the flexible substrate 110. For example, the sensor probe 120 could include optical fiber(s), flexible element(s) (e.g., an elongate piece of polyimide or other polymeric or metallic substance), wire(s), elongate pieces of shaped silicon, or other elements adhered, welded, bonded, or otherwise attached to the flexible substrate 110.

The sensor probe 120 could be configured to pierce skin to allow the sensor probe 120 to penetrate the skin and dispose the analyte sensor 125 and/or other elements disposed on the sensor probe 120 in contact with interstitial or other fluids within the skin. For example, the sensor probe 120 could be sharpened, or could include rigid materials (e.g., stainless steel tubes, rods, sheets, needles) to facilitate application of force to the sensor probe 120 to pierce the skin.

In some examples, the sensor probe 120 could include materials having a stiffness that changes to allow the sensor probe 120 to be used to pierce the skin during a first period of time and subsequently to become less rigid or to change some other property. For example, the sensor probe 120 could include a piece of poly-2-hydroxyethyl methacrylate (poly-HEMA) or some other hydrogel configured to soften by absorbing water (e.g., from interstitial fluid) once the sensor probe 120 has penetrated the skin. In another example, the sensor probe 120 could include a stiff material that is configured to dissolve into and/or be absorbed by the skin (e.g., polylactic acid (PLA)).

Additionally or alternatively, the sensor probe 120 could be inserted into skin by another device that is configured to pierce the skin, or into an incision into the skin formed by another device. For example, the sensor probe 120 could be configured to be mounted within the channel of a half-needle of a device configured to insert the sensor probe 120 into skin or to mount the flexible substrate 110 to a skin surface. The half-needle could pierce the skin and subsequently be retracted, leaving the sensor probe 120 in place penetrating the skin.

The depiction of a body-mountable sensor platform 100 having a single sensor probe 120 on a distal end of which a single analyte sensor 125 is disposed and having an optical sensor 127 disposed on a bottom surface 150 of a flexible substrate 110 is intended as a non-limiting, illustrative example. The body-mountable sensing platform 100 could include additional sensors disposed at different locations of the sensing platform (e.g., particular locations on a sensor probe). For example, the sensor probe 120 could include a plurality of sensors disposed along the length of the sensor probe 120 to allow for detection of some property of skin (e.g., a concentration of an analyte within the skin) at a variety of depths within the skin. The body-mountable sensor platform 100 could thus include more than one sensor probe and such sensor probes could have different widths, lengths, thicknesses, sensors, sensor locations, or other properties.

In examples, the sensor probe 120 could be configured to penetrate skin through a pre-existing cut, puncture, incision, or other entry through the surface of the skin into tissue (e.g., dermal tissue, subcutaneous tissue) containing a fluid of interest (e.g., interstitial fluid). Such a pre-existing entry could be formed for the purpose of inserting the sensor probe 120 by a lancet, needle, or other instrument configured to pierce the skin.

Figure 2A:
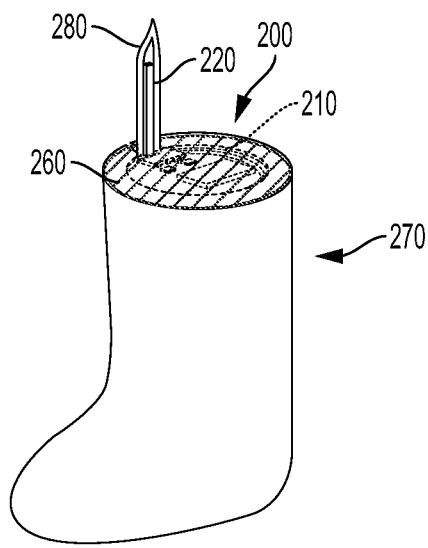
FIG. 2A is an aspect view of an example body-mountable device removably mounted to an example insertion device, in accordance with an example implementation.

FIG. 2A illustrates an example body-mountable sensing platform 200 removably mounted to an example insertion device 270, in accordance with an example implementation. The body-mountable sensing platform 200 is similar to the body-mountable sensing platform 100. The body-mountable sensing platform 200 includes a flexible substrate 210, a sensor probe 220 attached to the flexible substrate 210, and an adhesive layer 260 configured to adhere the flexible substrate 210 to a skin surface. The sensor probe 220 is configured to penetrate the skin and includes a sensor (not shown) disposed on the sensor probe 220 and configured to detect a property of the skin and/or to otherwise interact with tissues beneath and/or within the skin. For example, the sensor could be configured to detect an analyte (e.g., to measure a concentration of glucose) in a fluid within the skin (e.g., in interstitial fluid) when the sensor probe 220 penetrates the skin. The sensor probe 220 is coupled to a needle 280 of the insertion device 270. The needle 280 is a half-needle. That is, the needle 280 includes a channel along the length of the needle 280 in which the sensor probe 220 is disposed. The needle 280 is configured to pierce skin such that the needle 280 and the coupled sensor probe 220 penetrate the skin. That is, the needle 280 is sufficiently rigid and/or has an end that is sufficiently sharp to enable the needle 280 to pierce the skin. The insertion device 270 can then be moved away from the skin, and the needle 280 can be retracted while the sensor probe 220 remains inserted in (i.e., penetrating) the skin and the flexible substrate 210 remains mounted on the skin surface.

Figure 2B:
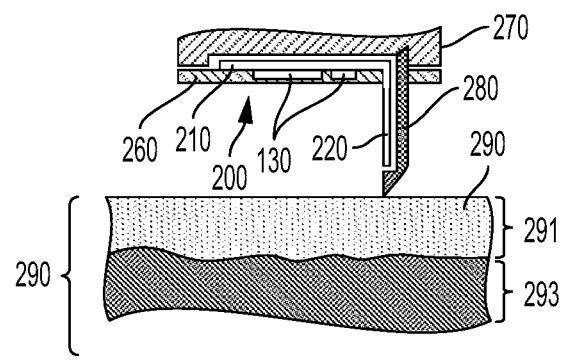
FIG. 2B is a cross-sectional view of the body-mountable device and insertion device of FIG. 2A, positioned proximate to skin of a living body, in accordance with an example implementation.
Figure 2C:
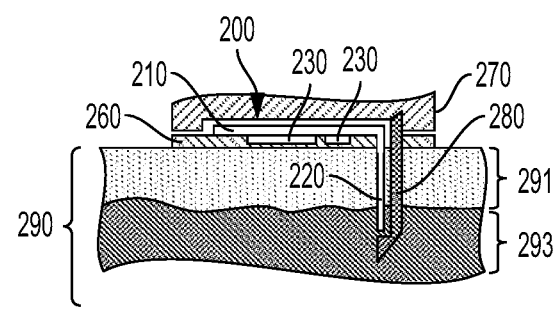
FIG. 2C is a cross-sectional view of the body-mountable device, insertion device, and skin of a living body of FIG. 2B, showing the body-mountable device and insertion device penetrating the skin, in accordance with an example implementation.
Figure 2D:
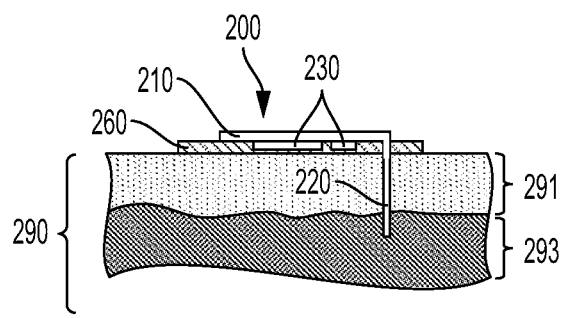
FIG. 2D is a cross-sectional view of the body-mountable device, insertion device, and skin of a living body of FIG. 2B, showing the body-mountable device penetrating the skin and the insertion device retracted from the skin, in accordance with an example implementation.

FIGS. 2B-2D show, in cross-section, the process of using the insertion device 270 to pierce skin 290. The skin 290 includes an epidermal layer 291 and a dermal layer 293. FIG. 2B shows the body-mountable sensing platform 200 removably mounted to the insertion device 270 such that the sensor probe 220 of the sensing platform 200 is coupled to the needle 280 of the insertion device 270. In this example, the sensor probe 220 is disposed within a channel of the needle 280. As shown in FIG. 2B, the insertion device 270 and the sensing platform 200 removably mounted thereto are disposed proximate the skin 290, but have not yet pierced the skin 290.

FIG. 2C shows the insertion device 270 and sensing platform 200 after the needle 280 (and the sensor probe 220 coupled thereto) has been inserted into the skin 290 (i.e., the needle 280 has pierced the skin). Further, the flexible substrate 210 has been mounted, via the adhesive action of the adhesive layer 260, to the skin 290 surface. The sensor probe 220 penetrates the skin 290 such that the distal end of the sensor probe 220 is located in the dermal layer 293 of the skin 290. In this manner, a sensor disposed on the end of the sensor probe 220 could detect an analyte in interstitial or other fluids present in the dermal layer 293.

FIG. 2D shows the sensing platform 200 after the needle 280 of the insertion device 270 has been retracted. The sensor probe 220 remains in place penetrating the skin 290 such that the distal end of the sensor probe 220 is located in the dermal layer 293 of the skin 290.

The illustrated insertion device 270 and the sensing platform 200 and use thereof to pierce and/or penetrate the skin 290, are intended as non-limiting illustrative examples of such devices and methods. The insertion device 270 and/or the sensing platform 200 could have different shapes, include different components and/or elements, be configured differently. For example, the insertion device 270 could consist of a disk to which a half-needle or other penetrating means are attached and to which a body-mountable sensing platform could be removably mounted. In some examples, the insertion device 270 could be configured to provide some additional functionality, e.g., could be configured to receive communications from the sensing platform 200 (e.g., to receive information related to the detected analyte). Other example additional functionality could include recharging the sensing platform 200 or activating the sensing platform 200.

In some examples, the insertion device 270 could include a driving mechanism such as a spring-loaded mechanism, a servomechanism including one or more solenoids, motors, or other electromechanical actuators. The driving mechanism may be configured to drive the needle 280 and the sensor probe 220 coupled thereto into skin to a specified depth within the skin, at a sufficiently high speed to minimize user discomfort). In some examples, the needle 280 could be retractable into the insertion device 270 for safety.

The mounting of body-mountable sensing platforms to skin surfaces of living bodies, and in some examples the penetration of such skin by sensor probes of sensing platforms, are intended as non-limiting illustrative examples of devices and methods described herein. Such devices and systems could be used to detect other properties of a body and/or of the environment of the devices and systems in some other way. This could include detecting analytes in or other properties of other tissues by penetrating such other tissues with sensor probes and/or mounting flexible substrates to surfaces of such tissues. For example, sensor probes, flexible substrates, and/or sensing platforms as described herein could be used to detect an analyte within a mucosal epithelium (e.g., within the mucosa of a mouth, nose, or other mucosa of a living body). Additionally or alternatively, sensor probes, flexible substrates, and/or sensing platforms as described herein could be used to detect analytes in a variety of fluids without penetrating tissues For instance, the sensing platforms could be used to detect an analyte in a tissue present in a volume of a living body, e.g., to detect an analyte in peritoneal fluid by disposing a sensing-platform as described herein within the peritoneal cavity of a living body.

A sensor disposed at a distal end of a sensor probe or at some other location of a body-mountable sensing platform as described herein could include a variety of components and/or substances configured in a variety of ways. In some examples, such sensors could include one or more substances that selectively interact with an analyte. For example, such substances could include proteins, enzymes, aptamers, DNA, RNA, nano-structures, antibodies, reagents, nano-structured surfaces, or other substances configured to selectively bind to, catalyze a reaction of, or interact with an analyte of interest. Such an analyte-sensitive substance could be disposed on a surface of a sensing platform (e.g., on a metal surface of an electrode, on a surface of an optical fiber, on some other surface of a sensor probe and/or flexible substrate). For instance, the analyte-sensitive substance on the surface may be cross-linked using glutaraldehyde.

Alternatively, the analyte-sensitive substance could be disposed within a polymer, gel, or other layer that is permeable to the analyte and that is disposed on such a surface. Such a polymer layer can be permeable to the analyte and contain a reagent that selectively reacts with the analyte to create a reaction product that can be sensed directly by an electrode. For instance, a fluorophore or other substance could selectively interact with the reaction product. In some examples, the polymer layer that contains the analyte-selective substance is a hydrogel that includes 2-hydroxyethyl methacrylate units. Such a hydrogel could contain additional polymer units or other chemicals to adjust a permeability of the hydrogel to the analyte. The additional polymer units could also bind the analyte-selective substance within the hydrogel, increase a degree of crosslinking of the hydrogel, or to specify one or more other properties of the hydrogel. For example, such a hydrogel could additionally include di(ethylene glycol) dimethacrylate units.

In some examples, the sensor of a sensing platform can include two or more electrodes configured to detect or measure the analyte electrochemically. The two or more electrodes could include a working electrode selectively sensitive to the analyte and a reference electrode. In some examples, exposing the sensor to a target fluid (e.g., interstitial fluid) causes a potentiometric voltage to develop between the working electrode and the reference electrode that can indicate the concentration of the analyte near the working electrode. Additionally or alternatively, a specified voltage could be applied between the reference electrode and the working electrode. An amount of current that responsively flows through the working electrode could be related to the concentration of the analyte near the working electrode. Alternatively, the current could be related to the rate at which the analyte diffuses to the working electrode (e.g., through a hydrogel layer containing an analyte-selective substance.

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Also, a color, saturation, absorption spectrum, or some other optical property of a substance disposed at the end of the sensor probe could be related to the presence, concentration, or some other property of the analyte.

The sensor platform could include a light emitter and/or a light detector configured to illuminate and to receive light emitted from the analyte-sensitive substance, respectively, in order to determine the optical property of the substance that is related to the analyte. In some examples, a sensor probe of the sensing platform could include an optical fiber and the analyte-selective substance could be disposed on a distal end of such an optical fiber. In such examples, a light emitter and/or a light detector could be disposed at a proximal end of the optical fiber. In this manner, the light emitter and light detector illuminate and receive light from the analyte-sensitive substance via the optical fiber. In examples, the light emitter and/or light detector could be disposed on a flexible substrate of the sensor platform (e.g., as part of electronics disposed on the flexible substrate).

In examples, an optical sensor could be configured to detect a reflectance spectrum, an absorbance spectrum, a fluorescence spectrum, an excitation spectrum, an emission spectrum, or some other spectral information or spectrum relating to optical properties of a tissue. Such an optical sensor could detect one or more optical properties related to the presence and/or amount of a substance (e.g., a concentration of hemoglobin in blood, a volume of blood in a portion of skin), a property of a substance (e.g., an oxygenation state of hemoglobin in blood). Such detected properties could be used to determine one or more properties of the skin to which the sensing platform is mounted and/or of a body comprising the skin. For example, an optical sensor could be configured and/or operated to detect an oxygenation of blood in the skin, a timing and/or frequency of pulses of blood in the skin and/or of heartbeats of the heart of the body comprising the skin, a degree of perfusion of the skin, or some other properties.

A body-mountable sensor platform could include additional or alternative sensors. Such sensors could include temperature sensors, accelerometers, gyroscopes, magnetometers, barometric pressure sensors, magnetic field sensors, electric field sensors, electromagnetic field sensors, or other types of sensors. Such sensors could be configured and/or operated to detect properties of skin to which the sensing platform is mounted and/or to detect properties of the environment of the sensing platform. A body-mountable sensing platform could include additional or alternative sensors and/or combinations thereof.

III. EXAMPLE ELECTRONICS OF A FLEXIBLE BIOSENSOR PLATFORM

Figure 3:
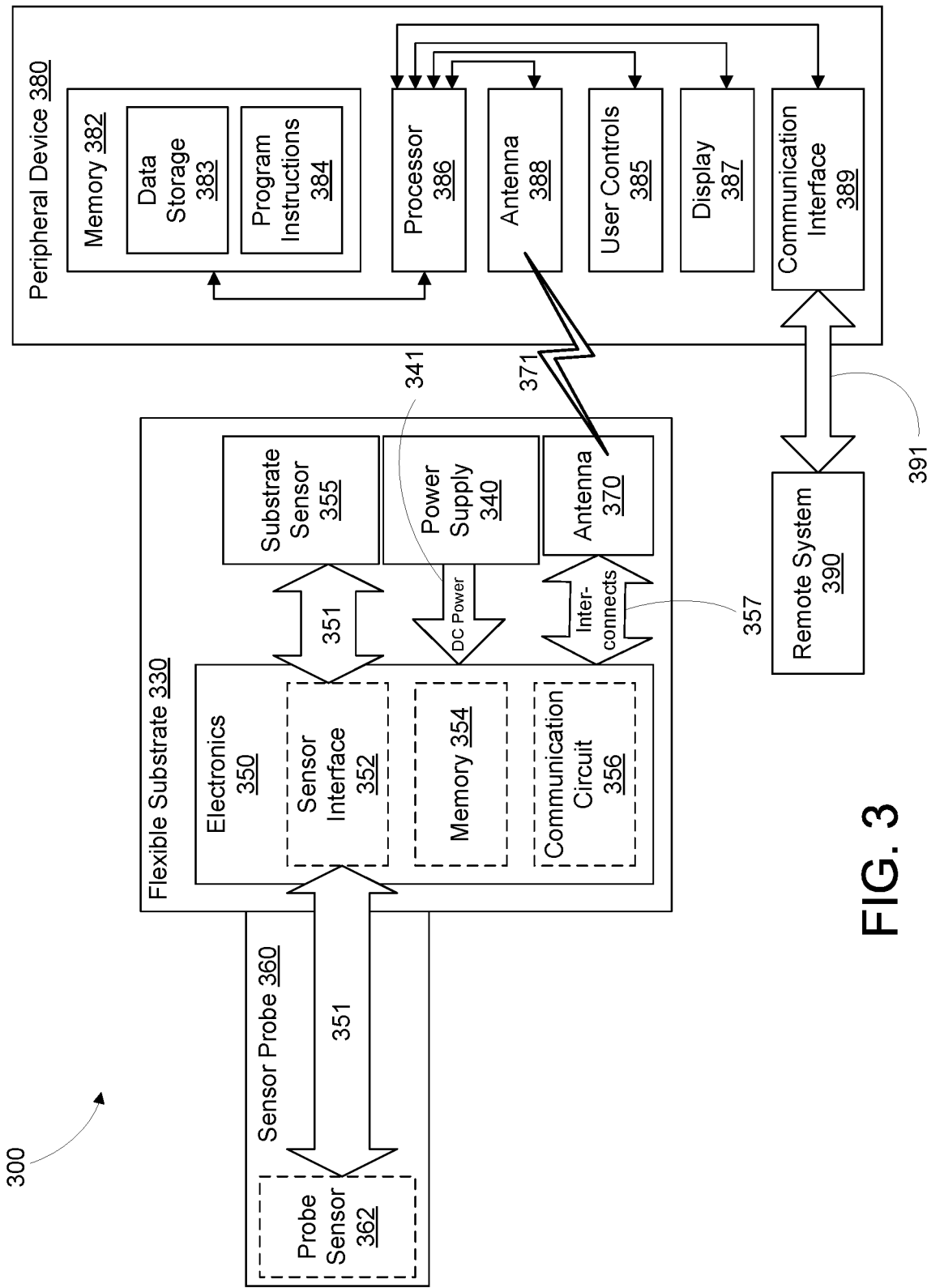
FIG. 3 is a block diagram of an example system that includes a body-mountable device in wireless communication with a peripheral device, in accordance with an example implementation.

FIG. 3 is a block diagram of a system that includes a body-mountable sensor platform 300 in wireless communication with a peripheral device 380. The body-mountable sensor platform 300 may, for example, represent the body-mountable sensor platforms 100 and 200 described above.

The body-mountable sensor platform 300 includes a flexible substrate 330 that is made of a flexible polymeric or metallic material formed to be mounted to a skin surface. The flexible substrate 330 provides a mounting surface for a power supply 340, electronics 350, substrate sensor 355, and a communication antenna 370. The power supply 340 supplies operating voltages to the electronics 350 and/or other elements of the sensing platform 300. The antenna 370 is operated by the electronics 350 to communicate information to and/or from the body-mountable sensing platform 300. The antenna 370, the electronics 350, substrate sensor 355, and the power supply 340 can all be situated on the flexible substrate 330.

Similar to the flexible substrates 110 and 210, the flexible substrate 330 and/or elements disposed thereon can have properties that enable the flexible substrate 330 to be mounted to a skin surface of a living body with minimal interference with activities of the living body. This could include the flexible substrate 330 being sufficiently flexible that mounting of the flexible substrate 330 to the skin surface causes a minimum of discomfort. The flexible substrate 330 could be composed of polyimide or some other flexible polymeric or other material.

One or more surfaces of the flexible substrate 330 could be used as a platform for mounting components including the antenna 370, the electronics 350, substrate sensor 355, and the power supply 340, chips, and conductive materials. The composition of the flexible substrate 330 could be specified such that metal contacts, traces, and interconnects can be patterned directly on the surface of the flexible substrate 330.

The electronics 350 disposed on the flexible substrate 330 could include a variety of devices. For example, the electronics 350 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 330. Further, antennas, electrodes, capacitors, resistors, analyte sensors, or other components could be formed from such traces or other interconnects formed on the surface of the flexible substrate 330. The electronics 350 can include logic elements configured to operate the substrate sensor 355 to detect a property, an antenna to wirelessly indicate information about the detected analyte, etc.

The body-mountable sensing platform 300 further includes a sensor probe 360 that is attached to the flexible substrate 330. The sensor probe 360, similar to the sensor probes 120 and 220, could be an elongate element of the body-mountable sensing platform 300 that is configured to penetrate a skin surface. In this manner, a probe sensor 362 located at a distal end of the sensor probe 360 is disposed within skin (e.g., in contact with interstitial fluid, blood, or some other fluid of interest) when the sensor probe 360 is penetrating the skin.

The flexible substrate 330 includes one or more surfaces suitable for mounting the electronics 350 (including a sensor interface 352, a memory 354, and a communication circuit 356), the power supply 340, the substrate sensor 355, and the antenna 370). The flexible substrate 330 can be employed both as a mounting platform for chip-based circuitry and/or as a platform for patterning conductive materials to create electrodes, interconnects, antennae, etc.

The power supply 340 is configured to provide energy to power the electronics 350. For example, the power supply 340 could include a battery. Such a battery could be flexible, e.g., the battery could be a flexible lithium-ion battery or some other type of flexible battery. The battery could be flexible to allow the flexible substrate 330 to which the battery is mounted to flex in response to deformation or motion of a skin surface to which the flexible substrate 330 is mounted. The battery could have a capacity sufficient to power the platform 300 for a protracted period of time, e.g., 18 hours, a week, or some other protracted period of time of periodic operation of the various components. For example, the battery could be a flexible battery with a capacity of more than approximately 60 microamp-hours and a thickness of less than approximately 0.5 millimeters.

In some examples, the power supply 340 could include a rechargeable battery and could further include some means for recharging such a battery. For example, the power supply 340 could include contacts disposed on a surface of the flexible substrate 330 and configured to receive electrical power from complimentary contacts of a charging device. In another example, the sensing platform 300 could include a loop antenna (e.g., a loop antenna comprising conductive traces patterned on the flexible substrate 330). In this example, the power supply 340 could be configured to use the loop antenna to receive RF energy from an external device (e.g., the peripheral device 380). In some examples, such an RF-energy-receiving antenna could be the same antenna as the antenna 370 used to communicate with external devices.

The sensor interface module 352 and connections 351 between the sensor interface module 352 and the sensors 355, 362 could take a variety of forms according to the methods used to detect a physiological property (e.g., an analyte in interstitial fluid). The sensors 355 and 362 are similar the sensors 125 and 127 described above, for example. One or both of the sensors 355, 362 can include an analyte-selective substance that selectively interacts with the analyte in a fluid (e.g., interstitial fluid in skin, sweat on the surface of the skin). The sensor(s) 355, 362 and sensor interface 352 can then detect the selective interaction between the analyte and the analyte-selective substance to detect a presence and properties of the analyte.

Such detection can include detecting the interaction between the analyte and the analyte-selective substance directly (e.g., by detecting a change in an optical property of the analyte-selective substance) or indirectly (e.g., by detecting a reaction product of the selective reaction of the analyte. Direct or indirect detection of the analyte could include electrochemical detection, optical detection, or some other detection means.

The memory 354 could include a variety of volatile and nonvolatile electronic storage elements configured to provide means for the sensing platform 300 to record and/or log detected information about the analyte. For example, the memory 354 could include one or more EEPROM memories, flash memories, NVRAM memories, DRAM memories, SRAM memories, flip-flops, or other information storage elements. The memory 354 could have an information storage capacity sufficient to record some specified period of detected information at some specified rate of detection. For example, the memory 354 could have a capacity sufficient to record more than 18 hours, a week, or some other protracted period of time of detected information (e.g., concentrations of an analyte) when detected at a rate of approximately once per minute. Additionally or alternatively, the sensing platform 300 could be in communication with a memory that is external to the sensing platform 300 and that could be used as described above with respect to the memory 354.

The electronics 350 include a communication circuit 356 for sending and/or receiving information via the antenna 370. The communication circuit 356 can optionally include one or more oscillators, mixers, frequency injectors, etc. to modulate and/or demodulate information on a carrier frequency to be transmitted and/or received by the antenna 370. In some examples, the body-mountable sensing platform 300 is configured to indicate information (e.g., detected analyte concentrations) by modulating an impedance of the antenna 370 in a manner that is perceivable by the peripheral device 380. For example, the communication circuit 356 can cause variations in the amplitude, phase, and/or frequency of backscatter radiation from the antenna 370, and such variations can be detected by the reader 380. Such wireless communication could be compatible with one or more existing backscatter wireless communications standards, e.g., RFID. Additionally or alternatively, the communication circuit 356 and antenna 370 could be configured to transmit wireless signals according to some other method, e.g., according to the Bluetooth (e.g., Bluetooth Low Energy), ZigBee, WiFi, LTE, and/or some other wireless communications standard. In some examples, such communications (e.g., data transmitted from the sensor platform 300, operational instructions transmitted to the sensor platform 300) could be cryptographically secured.

In an example, the communication circuit 356 and the antenna 370 may be associated with an NFC transmitter coupled to the flexible substrate 330. The NFC transmitter could be configured to communicate information related to a measurement made by the sensor(s) 355, 362 to the peripheral device 380. The communicated information could include stored information (e.g., analyte concentration values detected using the probe sensor 362 at a plurality of past points in time and stored in the memory 354). In some examples, the communicated information could include information related to an information link between the body-mountable sensing platform 300 and the peripheral device 380. For example, the communicated information could include a request for further communication and/or a request for information about a communications protocol. For instance, the communicated information could include information related to linking the body-mountable sensing platform 300 with the peripheral device 380 by way of NFC pairing between the platform 300 and the peripheral device 380. Further, the communicated information could include security information (e.g., cryptographic keys, passwords) related to securing further communication between the body-mountable sensing platform 300 and the peripheral device 380.

Generally, NFC involves a technology that enables devices to establish radio communication with each other by touching the devices together or bringing them into proximity to a distance of typically 10 cm (3.9 in) or less. NFC may employ electromagnetic induction between two loop antennae when NFC devices (e.g., the NFC transmitter of the flexible substrate 300 and the peripheral device 380) exchange information. NFC enables the devices to operate within the globally available radio frequency industrial, scientific, and medical (ISM) band of 13.56 Mega Hertz (MHz). Further, NFC enables the devices to operate on International Organization for Standardization (ISO)/International Electrotechnical Commission (IEC) 18000-3 air interface and at rates ranging from 106 kbit/s to 424 kbit/s.

An NFC device can work in three modes: NFC Target; NFC Initiator; and NFC peer-to-peer. An NFC initiator actively generates a radio frequency (RF) field that can power a passive NFC target (an unpowered chip) commonly referred to as a "tag." NFC peer-to-peer communication differs in application as both devices (peers) are powered. For instance, both the NFC transmitter coupled to the flexible substrate 330 and the peripheral device 380 may be powered, and thus represent peer-to-peer NFC communication. In examples, NFC standards cover communications protocols and data exchange formats and may be based on radio-frequency identification (RFID) standards including ISO/IEC 14443. The standards include ISO/IEC 18092.

In another example, in addition or alternative to the NFC transmitter, the communication circuit 356 and the antenna 370 may be associated with a BLE transmitter coupled to the flexible substrate 330. BLE is a wireless personal area network technology. Compared to Classic Bluetooth, BLE provides reduced power consumption and cost while maintaining a similar communication range.

BLE may operate in the same spectrum range (e.g., the 2.400 GHz-2.4835 GHz band) as classic Bluetooth technology, but may use a different set of channels. Instead of the Classic Bluetooth 79 1-MHz channels, BLE may have 40 2-MHz channels. Within a channel, data is transmitted using Gaussian frequency shift modulation, similar to classic Bluetooth. The bit rate may be about 1 Mbit/s, and the maximum transmit power may be about 10 milli Watt. BLE may use frequency hopping to counteract narrowband interference problems. Particularly, BLE uses digital modulation techniques or a direct-sequence spread spectrum in implementing frequency hopping.

BLE may enable low power consumption by the sensing platform 300. This is possible because of BLE's power-efficient communication protocol. Particularly, BLE intermittently transmits small packets of data as opposed to continuous scanning and transmission of data as implemented by classic Bluetooth technology and other types of transmitters.

In examples, the sensing platform 300 may include both an NFC transmitter and a BLE transmitter. Each transmitter may be configured to transmit different types of data.

The sensor interface 352 is connected to the sensor(s) 355, 362 via sensor interconnects 351. In some examples, the sensor interconnects 351 could include a patterned conductive material to connect components of the sensor 355 and 362 to a terminal on a microcontroller or other component(s) comprising the sensor interface 352. Additionally or alternatively, the sensor interconnects 351 could include an optical fiber or other means for transmitting light between the sensor(s) 355, 362 and the sensor interface 352. For example, the sensor interface 352 could comprise a light emitter and/or light detector and the sensor(s) 355, 362 could include an analyte-sensitive substance that has an optical property that is related to a property of the analyte. In such examples, the light emitter and/or a light detector could be disposed at a proximal end of the optical fiber. In this case, the light emitter and light detector illuminate and receive light from the analyte-sensitive substance via the optical fiber of the sensor interconnects 351. Similarly, the electronics 350 are connected to the antenna 370 via interconnects 357. Other configurations of the sensor interconnects 351 and 357 are anticipated (e.g., capillary tubes, microfluidic elements, etc.).

The block diagram shown in FIG. 3 is described in connection with functional modules for convenience in description. However, embodiments of the body-mountable sensing platform 300 can be arranged with one or more of the functional modules ("sub-systems") implemented in a single chip, integrated circuit, and/or physical feature or on multiple such elements.

The peripheral device 380 includes an antenna 388 (or group of more than one antenna) to send and receive signals by way of wireless link 371 to and from the body-mountable sensing platform 300. The peripheral device 380 also includes a computing system with a processor 386 in communication with a memory 382. The peripheral device 380 can also include one or more of user controls 385, a display 387, and a communication interface 389.

The memory 382 is a non-transitory computer-readable medium that can include, without limitation, magnetic disks, optical disks, organic memory, and/or any other volatile (e.g. RAM) or non-volatile (e.g. ROM) storage system readable by the processor 386. The memory 382 can include a data storage 383 to store indications of data, such as sensor readings (e.g., acquired using the sensors 355, 362), program settings (e.g., to adjust behavior of the body-mountable sensing platform 300 and/or peripheral device 380), etc. The memory 382 can also include program instructions 384 for execution by the processor 386 to cause the peripheral device 380 to perform processes specified by the instructions 384. For example, the program instructions 384 can cause the peripheral device 380 to perform any of the function described herein. For example, program instructions 384 may cause the peripheral device 380 to provide a user interface that allows for retrieving information communicated from the body-mountable sensing platform 300. The user interface may, for example, display that information on the display 387 in response to commands input through the user controls 385.

The peripheral device 380 can also include one or more hardware components for operating the antenna 388 to send and receive signals via the wireless link 371 to and from the body-mountable sensing platform 300. For example, oscillators, frequency injectors, encoders, decoders, amplifiers, filters, etc. can drive the antenna 388 according to instructions from the processor 386. In an example, the antenna 388 could be associated with an NFC transceiver or a BLE transceiver. In examples, the peripheral device 380 may include both an NFC transceiver and a BLE transceiver.

The peripheral device 380 can be a smart phone, digital assistant, or other portable computing device with wireless connectivity sufficient to provide the wireless link 371. The peripheral device 380 can also be implemented as an antenna module that can be plugged into a portable computing device, such as in an example where the wireless link 371 operates at carrier frequencies not commonly employed in portable computing devices. In some instances, the peripheral device 380 is a special-purpose device configured to be periodically placed relatively near the sensing platform 300 to allow the wireless link 371 to operate with a low power budget.

For example, the sensing platform 300 may include an NFC transmitter (e.g., the communication circuit 356 and the antenna 370) and the peripheral device 380 may include an NFC receiver (e.g., the antenna 388). In this example, the peripheral device 380 is brought within NFC range from the NFC transmitter to receive information from the therefrom. Such intermittent NFC between the NFC transmitter and the peripheral device 380 may require a reduced amount of electrical power compared to other wireless communication protocols or setups.

In another example, the sensing platform 300 may include both an NFC transmitter and a BLE transmitter. The BLE transmitter may have a longer range than the NFC transmitter. Thus, the NFC transmitter may be configured to provide data encryption information, provide sensor initialization information (e.g., powering a sensor on, providing configuration settings, etc.), transfer sensor calibration information, provide pairing information with the peripheral device, etc., when the peripheral device 380 is brought within NFC range from the NFC transmitter. The BLE transmitter, on the other hand, may be configured to transmit sensor data to the peripheral device 380 intermittently. In an example, the BLE transmitter may transmit portions of sensor data or compression of data sets, while the NFC transmitter may transfer complete data sets.

The peripheral device 380 can also be configured to include a communication interface 389 to communicate signals via a communication medium 391 to and from a remote system 390. For example, the remote system 390 may be a drug delivery device, a smart phone, tablet computer, laptop computer, or personal computer. The communication interface 389 and the communication medium 391 may, for example, be a Bluetooth module and wireless Bluetooth communication signals, respectively. In this example, the peripheral device 380 may be configured to send information about measured physiological properties collected using the sensor(s) 355, 362 to the remote system 390 for storage, offline analysis, and/or further action such as adjusting a drug dosage. In some examples, the peripheral device 380 is embedded in the remote system 390. For instance, the peripheral device 380 may be a controller embedded within an insulin delivery pump represented as the remote system 390.

In an example where the body-mountable sensing platform 300 has been mounted to skin of a living body such that the probe 362 is in contact with interstitial fluid of the living body, the sensing platform 300 can be operated to detect an analyte in the interstitial fluid. Interstitial fluid is an extravascular fluid that suffuses many of the tissues of a living animal body. The interstitial fluid is continuously replenished by the blood supply through capillaries in the structure of tissue (e.g., dermal tissue, subcutaneous tissue). The interstitial fluid thus includes many biomarkers found in blood that are analyzed to characterize a person's health condition(s). For example, the interstitial fluid includes urea, glucose, calcium, sodium, cholesterol, potassium, phosphate, other biomarkers, etc. The biomarker concentrations in the interstitial can be systematically related to the corresponding concentrations of the biomarkers in the blood, and a relationship between the two concentration levels can be established to map interstitial fluid biomarker concentration values to blood concentration levels. Thus, measuring interstitial fluid analyte concentration levels using sensing platforms as described herein can provide a technique for monitoring analyte levels. This technique is more efficient compared to blood sampling techniques performed by lancing a volume of blood to be analyzed outside a person's body. Moreover, the body-mountable sensor platform disclosed herein can be operated substantially continuously to enable real time measurement of analyte concentrations or other information about an analyte.

In some implementations, the body-mountable sensing platform 300 can operate to non-continuously ("intermittently") indicate information related to a physiological property (e.g., concentration values of an analyte in interstitial or other fluids). For example, the body-mountable sensing platform 300 could periodically operate the probe sensor 362 to detect an analyte and to store information related to the detection of the analyte in the memory 354. The sensing platform 300 could then less frequently operate to transmit stored information relating to more than one detection of the analyte or other physiological property. Additionally or alternatively, a user could operate the peripheral device 380 to request such information transmission by the sensing platform 300. For instance, when a reading is desired, the peripheral device 380 may be brought within proper range (e.g., range suitable for NFC transmission) to obtain a reading of an analyte concentration.

In another example, the sensing platform 300 could provide an indication to a user (e.g., via a light, vibration motor, or other user interface element(s) of the output component 320) that the user should operate the peripheral device 380 to receive such transmitted information. The indication may be provided due to, for example, the memory 354 being nearly full or a battery of the power supply 340 being nearly depleted.

Body-mountable sensing platforms as described herein could be mounted to skin at a variety of different locations of a body. Such locations could be selected to provide access to a particular portion of skin and/or a particular type or portion of tissue (e.g., to provide access to a portion of subsurface vasculature). Such locations could be selected to minimize discomfort caused by the sensing platform being mounting to skin for a protracted period of time. For example, the sensing platform could be mounted to a portion of skin that includes fewer nerve endings and/or that is minimally strained during the performance of activities of daily living. Such locations could include locations on the arms or abdomen of a user.

Figure 4:
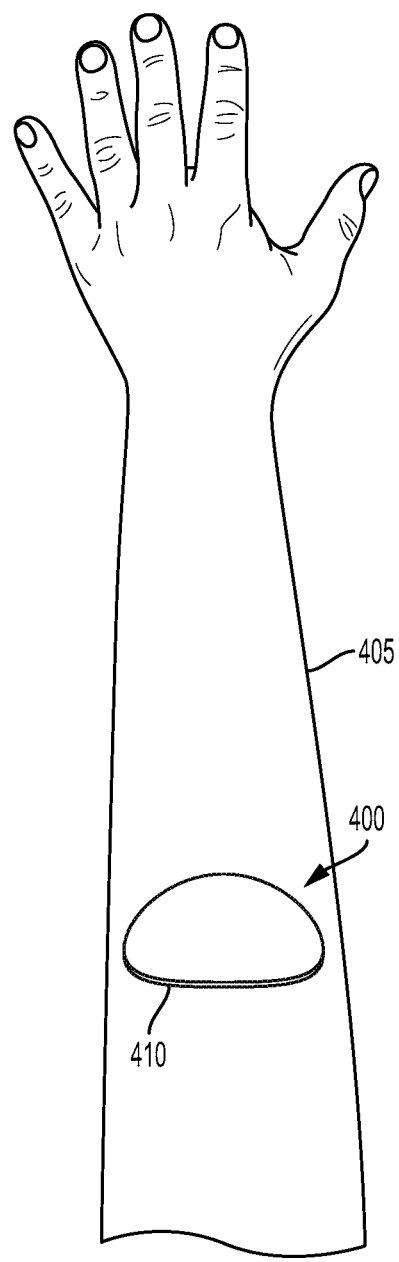
FIG. 4 is an aspect view of an example bandage-type body-mountable device mounted to a body, in accordance with an example implementation.

FIG. 4 illustrates such a location, showing a bandage-type body-mountable sensing platform 400 mounted to skin of an arm 405. The body-mountable sensing platform 400 represents any of the platforms 100, 200, and 300 described above.

The body-mountable sensing platform 400 includes a flexible substrate 410 configured to be mounted to a skin surface of the forearm of the arm 405. Sensors, electronics, transmitter, batteries, and/or other components could be disposed on or within the flexible substrate 410 to provide functions of the sensing platform 400. As described above, such functions may include detection of one or more physiological properties of skin to which the sensing platform 400 is mounted, e.g., a concentration of an analyte in interstitial fluid within the skin.

The flexible substrate 410 and the sensing platform as a whole 400 are sufficiently flexible that the sensing platform 400 deforms (i.e., curves) according to the surface of the skin to which the flexible substrate 410 is mounted. Additionally or alternatively, one or more components of the sensing platform 400 could be rigid and shaped and/or sized such that, when disposed on the flexible substrate 410, the sensing platform 400 as a whole deforms according to the surface of the skin to which the flexible substrate 410 is mounted.

The particular body-mountable sensing platforms, configurations, and operations thereof illustrated herein (e.g., as body-mountable sensing platforms 100, 200, 300, 400) are intended as non-limiting examples. Differently-configured sensing platforms (e.g., having differently-shaped and/or sized flexible substrates or other components), or other properties of the configuration and operation of body-mountable sensing platforms are contemplated.

The following control system description uses glucose level control as an example for illustration. However, a similar system can be implemented to control other physiological properties as well.

IV. EXAMPLE GLUCOSE LEVEL CONTROL SYSTEM

Diabetes patients may take insulin medications to control high glucose levels to prevent hyperglycemia, which is a condition that occurs when an excessive amount of blood sugar (glucose) circulates in the blood plasma (e.g., glucose level above 200 milligram/deciliter). However, inaccurate control of insulin medication amounts taken by a patient may cause hypoglycemia, which is a condition that occurs when glucose is below a certain level (e.g., 70 milligram/deciliter). Hyperglycemia and hypoglycemia are both harmful to the patient. A closed loop feedback control of patient glucose levels that is configured to control an insulin delivery device based on continuous monitoring of glucose levels may facilitate maintaining the glucose level between target values to prevent both hyperglycemia and hypoglycemia.

Figure 5:
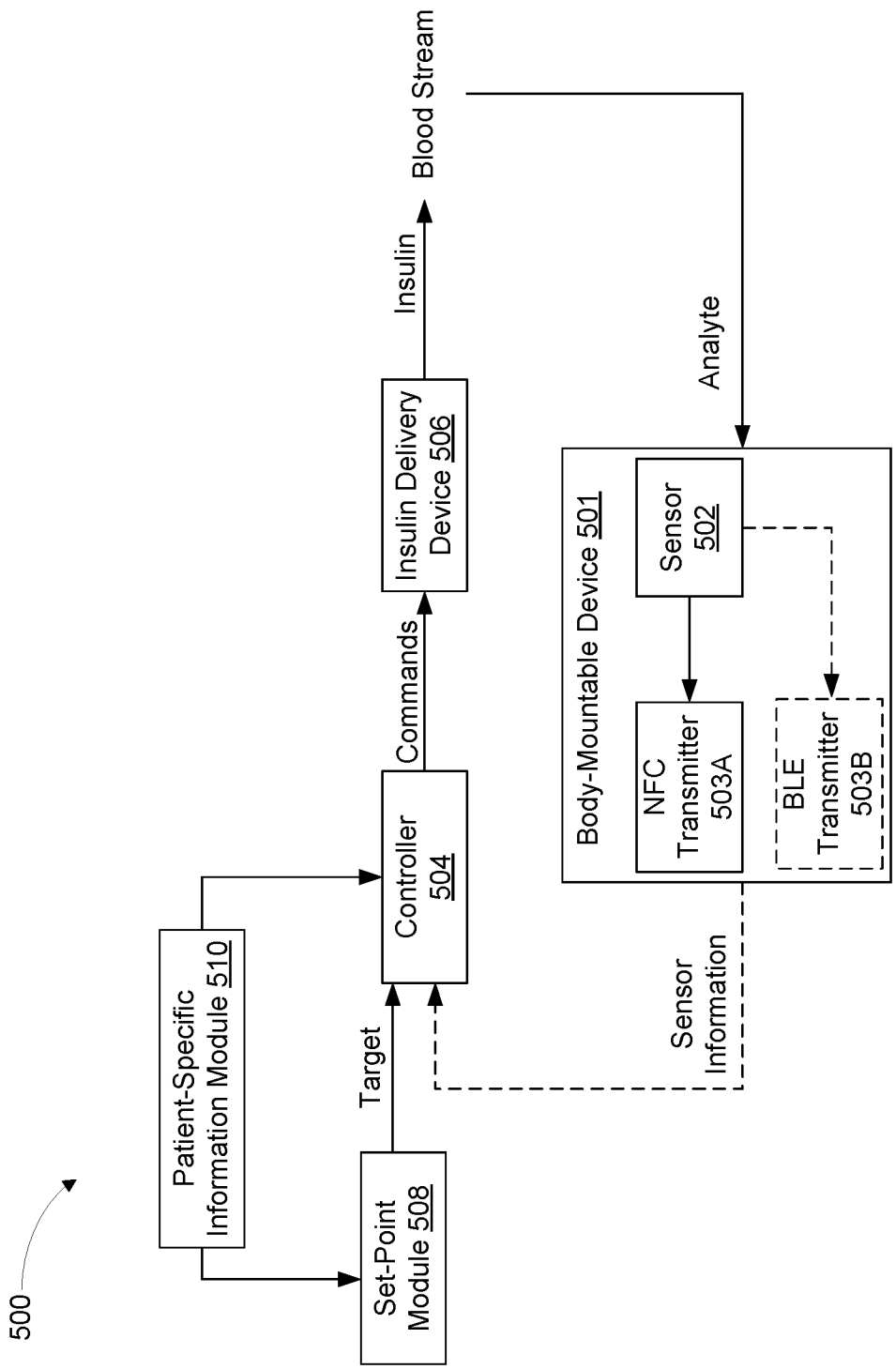
FIG. 5 is a block diagram of a glucose control system, in accordance with an example implementation.

FIG. 5 is a block diagram of a glucose control system 500, in accordance with an example embodiment. FIG. 5 depicts a body-mountable device 501 mounted on a skin surface similar to the body-mountable devices 100, 200, 300, and 400 described above. The body-mountable device 501 includes a glucose sensor 502 and an NFC transmitter 503A. The body mountable device 501 may also include a BLE transmitter 503B. The BLE transmitter is shown as a block having dashed line to indicate that one transmitter (e.g., the NFC transmitter 503A) may be sufficient, but that in alternative configuration more than one transmitter might be used to transmit different types of data. For instance, one transmitter may be configured to provide encryption data, pairing information, sensor calibration information, etc., while the other transmitter provides sensor measurements. Each transmitter may transmit data intermittently, and the frequency of transmission may be different as well. For instance, the NFC transmitter 503A may provide data when a peripheral device or a controller is within NFC range, whereas the BLE transmitter 503B may provide data more frequently.

Further, the body-mountable device 501 is in communication with a controller 504. The controller 504 may represent the peripheral device 380 described above, for example. The controller 504 communicates with the body-mountable device 501 when the controller 504 is within a predetermined threshold distance from the body-mountable device 501. The two devices being within the predetermined threshold distance from each other enables communication therebetween by way of the NFC transmitter 503A and/or the BLE transmitter 503B.

The controller 504 is configured to control an insulin delivery device 506, which is configured to inject insulin into a blood stream. The controller 504 may have access to a set-point module 508 and a patient-specific information module 510. The set-point module 508 may also be in communication with the patient-specific information module 510.

The sensor 502, similar the sensor 125 for example, may be disposed on a sensor probe configured to penetrate a skin surface to contact a fluid (e.g., interstitial fluid, blood) containing an analyte of interest. In this case, the analyte of interest is glucose. The sensor 502 may be an electrochemical glucose sensor configured to measure glucose concentration, for example.

The sensor 502 may further provide one or more sensor measurements to the NFC transmitter 503A (or the BLE transmitter 503B), and the NFC transmitter 503A may in turn provide information related to the sensor measurements to the controller 504. In an example, the NFC transmitter 503A may continuously provide the information to the controller 504. In another example, to save electric power used to operate the NFC transmitter 503A, the NFC transmitter 503A may be configured to operate as a passive short range transmitter. In this manner, the NFC transmitter 503A may provide the information to the controller 504 when the controller 504 is within proper range (i.e., range suitable for NFC). The NFC transmitter 503A may, for example, detect the controller 504 being within the range, or receive information or an indication from another device that the controller 504 is within range and is seeking the information. This way, the NFC transmitter 504 can be made small in size enabling the body-mountable device 501 to be small and comfortable to wear or attach to skin. Further, in this case, the NFC transmitter 503A may consume low amount of power from a battery of the body-mountable device 501 to operate, thus the battery may last longer.

In another example, the body-mountable device 501 may include both the NFC transmitter 503A and the BLE transmitter 503B to transmit different types of information. The BLE transmitter 503B may have a longer range than the NFC transmitter 503A. Thus, the NFC transmitter 503A may be configured to provide information such data encryption information when the peripheral device 380 is brought within NFC range from the NFC transmitter, while the BLE transmitter 503B may be configured to transmit sensor data from the sensor 502 to the controller 504 intermittently. Such configuration may reduce power consumption associated with data transmission in general. In the description below, the NFC transmitter 503A is used to describe operation of the glucose control system 500. However, such description is not limiting, and in other contemplated implementations the BLE transmitter 503B could be used alternative to or in addition to the NFC transmitter 503A.

The controller 504 may include or be coupled to an NFC receiver to receive indications of one or more sensor measurements provided by the NFC transmitter 503A. In examples, the controller 504 may be configured such that if the controller 504 does not receive signals from the NFC transmitter 503A, the controller 504 provides an alert to a user. In response, the user may bring the controller 504 sufficiently close (i.e., within the predetermined threshold distance that enables NFC) to the NFC transmitter 503A so as to receive the information. Sensor measurements may be stored on a memory (such as the memory 354) until communication is established between the NFC transmitter 503A and the controller 504. Upon establishing communication when the two devices are within proper range of each other, the NFC transmitter 503A provides stored information to the controller 504.

In an example, the NFC transmitter 503A may be configured to periodically communicate the information related to the one or more sensor measurements to the controller without receiving commands or indications from the controller 504. In this example, the NFC transmitter 503A is a one way communication device that does not receive signals. This configuration may enable the NFC transmitter 503A to be small and consume less power. The controller 504 may receive the information if the controller 504 is within the proper distance from the NFC transmitter 503A. The controller 504 may provide an alert to the user after a particular period of time lapses without receiving the information from the NFC transmitter 503A.

The controller 504 may then determine blood glucose level based on the information indicative of the sensor measurements. The controller 504 may then generate instructions or commands that are communicated to the insulin delivery device 506 (e.g., any type of insulin pumps). In examples, the controller 504 may communicate the commands to the insulin delivery device 506 wirelessly using any available wireless protocol or via a wired connection. The insulin delivery device 506 may receive the commands and infuse insulin into the blood stream in response to the commands.

In examples, the controller 504 may include electrical components and software to generate the commands for the insulin delivery device 506. The controller 504 may also include a controller communication system to receive information from the NFC transmitter 503A and provide the commands to the insulin delivery device 506.

In an example, the controller 504 may include a user interface and/or operator interface (not shown) comprising a data input device and/or a data output device. The data output device may, for example, generate signals to initiate an alarm and/or include a display or printer for showing status of the controller 504 and/or a patient's vital indicators. The data input device may comprise dials, buttons, pointing devices, manual switches, alphanumeric keys, a touch-sensitive display, combinations thereof, and/or the like for receiving user and/or operator inputs. Other input and output device are possible as well.

The controller 504 may also obtain a target glucose level from the set-point module 508 and/or the patient-specific information module 510. The set-point module 508 may be configured to provide the target glucose level to the controller 504 based on stored information. In an example, the set-point module 508 may be configured to continuously adjust the target level based on information received from the patient-specific information module 510. For example, every patient may be different and may have a different target level appropriate for the patient's condition. The patient-specific information module 510 may be configured to store the patient's information (e.g., based on inputs by patient or physician treating patient with permission from the patient). The patient's information may include age, previous history of treatment, information related to history of response of patients to dosages of insulin, and any other relevant information. The patient-specific information module 510 may continuously be updated with new information over time. The set-point module 508 in communication with the patient-specific information module 510 may thus adjust the target glucose level based on any patient-specific information or updates thereof.

The controller 504 may be configured to compare the target glucose level to current blood glucose level determined based on information received or fed back from the NFC transmitter 503A. Based on the comparison, the controller 504 may be configured to provide the commands to the insulin delivery device 506. For example, the controller 504 may be configured to implement any form of close loop control techniques such as proportional, integral, derivative (PID) control, robust control, model-predictive control, adaptive control, etc. The controller 504 may thus generate the commands based on a discrepancy between the current blood glucose level and the target glucose level. An example adaptive controller 504 may be configured to include a learning algorithm that monitors patient response to doses of insulin over time and takes into consideration information provided by the patient-specific information module 510. Based on such information, the controller 504 may adapt or tailor the commands for enhanced control of glucose level in the blood stream of a specific patient.

In an example, the controller 504 may be configured to receive information related to the sensor measurements over time and establish a pattern of change or a rate of change of glucose concentration in the blood stream. The rate of change of glucose concentration may be indicative of a patient's response to insulin injections over time, for example. The rate of change may also be indicative of other health conditions of the patient. In this example, the controller 504 may be configured to establish the rate of change of glucose concentration and take the establish rate into consideration when providing the commands to the insulin delivery device.

In another example, in addition to establishing the target glucose concentration, the set-point module 508 may be configured to establish a range of glucose concentration about the target glucose concentration that may be considered healthy for a given patient. For instance, the range may be fixed or may be based on patient-specific information received from the patient-specific information module 510. In this example, the controller 504 may be configured to provide the commands such that the insulin delivery device 506 maintains a predetermined insulin delivery rate when the glucose concentration is within the established range. If the glucose concentration deviates from the range, the controller 504 may be configured to provide the commands such that the insulin delivery device 506 changes the insulin delivery rate to the blood stream so as to bring the glucose concentration in the blood stream within the range.

The insulin delivery device 506 may include an infusion device and/or an infusion tube to infuse insulin into the blood stream at a given rate. For example, the controller 504 may provide the commands to the insulin delivery device 506 to control the insulin delivery rate/dosages over time. In examples, insulin may be infused using an intravenous system for providing fluids to a patient (e.g., in a hospital or other medical environment).

In examples, an infusion device (not explicitly identified in FIG. 5) may include infusion electrical components to activate an infusion motor according to the commands, an infusion communication system to receive the commands from the controller 504, and an infusion device housing (not shown) to hold the infusion device.

In some examples, the controller 504 may be housed in the infusion device housing, and an infusion communication system may comprise an electrical trace or a wire that carries the commands from the controller 504 to the infusion device. Thus, the controller 504 and the insulin delivery device 506 may be co-located or integrated together. For instance, the controller 504 may take the form of a chip including hardware and software and located in the insulin delivery device 506. In this example, an NFC receiver may be coupled to the insulin delivery device 504 and configured to receive the information related to the one or more sensor measurements from the NFC transmitter 503A. The controller 504 thus receives the information by way of the NFC receiver coupled to the insulin delivery device 506.

In other examples, the controller 504 may have its own housing or may be included in a supplemental device. For instance, the controller 504 may be integrated into a mobile phone (e.g., an application installed on the mobile phone), a wearable computing device worn by the patient, a laptop or desktop in wired or wireless communication with the body-mountable device 501 and the insulin delivery device 506, etc.

In still another example, the controller 504 may be located at a remote server in wireless communication (e.g., using WiFi, CDMA, WiMAX, GSM, etc. interfaces) with the body-mountable device 501 and the insulin delivery device 506. In further examples, components of the system 500 such as the body-mountable device 501, the controller 504, and the insulin delivery device 506 may utilize a cable, a wire, a fiber optic line, radio frequency, infrared signals, or ultrasonic transmitters and receivers, or a combination thereof for communication with each other.

The system 500 thus illustrates a closed loop feedback control of patient glucose levels based on monitoring of glucose levels. In this manner, the control system 500 may facilitate maintaining the glucose level between target values to prevent both hyperglycemia and hypoglycemia.

Components of the system 500 may be configured to work in an interconnected fashion with each other and/or with other components coupled to respective systems. One or more of the described functions, components, or blocks of the system 500 may be divided up into additional functional or physical components, or combined into fewer functional or physical components. For example, the set-point module 508 may be integrated into the controller 504. The controller 504 may be integrated into the insulin delivery device 506. In this case, the NFC transmitter 503A may be communicating directly with an NFC receiver at the insulin delivery device 506.

In some further examples, additional functional and/or physical components may be added to the examples illustrated by FIG. 5. For example, the system 500 may include a filter (or a pre-filter) configured to filter and process signals from the sensor before the signals are provided to the controller 504. The system 500 may include a processor (e.g., a microprocessor, a digital signal processor (DSP), etc.) configured to execute program code including one or more instructions for implementing logical functions described with respect to the controller 504. The system 500 may further include any type of computer readable medium (non-transitory medium) or memory, for example, such as a storage device including a disk or hard drive, to store the program code. In other examples, the system 500 may be included within other systems.

V. EXAMPLE METHODS

Figure 6:
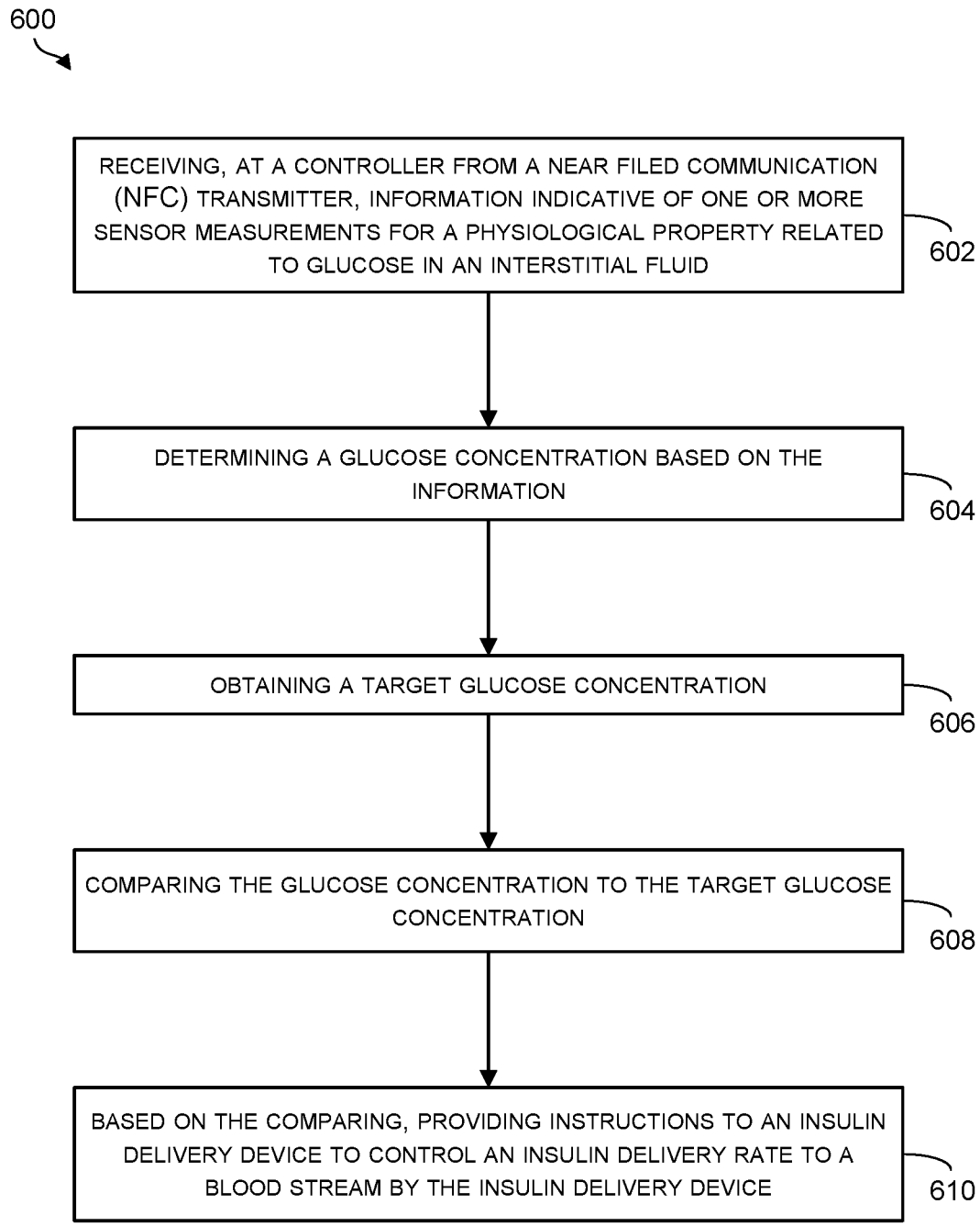
FIG. 6 is a flowchart of an example method for control of a peripheral device with a bandage-type analyte sensor, in accordance with an example implementation.

FIG. 6 is a flow chart of a method 600 for control of a peripheral device with a bandage-type analyte sensor, in accordance with an example implementation. The method 600 may include one or more operations, or actions as illustrated by one or more of blocks 602-610. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 600 and other processes and methods disclosed herein, the flowchart shows operation of one possible implementation of present examples. In this regard, each block may represent a module, a segment, or a portion of program code, which includes one or more instructions executable by a processor or a controller for implementing specific logical operations or steps in the process. The program code may be stored on any type of computer readable medium or memory, for example, such as a storage device including a disk or hard drive. The computer readable medium may include a non-transitory computer readable medium or memory, for example, such as computer-readable media that stores data for short periods of time like register memory, processor cache and Random Access Memory (RAM). The computer readable medium may also include non-transitory media or memory, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example. In addition, for the method 600 and other processes and methods disclosed herein, each block in FIG. 6 may represent circuitry that is wired to perform the specific logical operations in the process.

Further, the method 600 is described using an NFC transmitter. However, as described above, in addition or alternative to the NFC transmitter, a BLE transmitter may be used to transmit sensor information to a controller.

At block 602, the method 600 includes receiving, at a controller from an NFC transmitter, information indicative of one or more sensor measurements of a physiological property related to glucose in an interstitial fluid. The controller may be a computing device comprising one or more processors configured to execute program instructions stored in the computing device (e.g., a memory within the computing device), for example. In an example, the controller may be represented by hardware or software embedded in the peripheral device 380 described above.

The NFC transmitter is attached to a flexible substrate mounted to a skin surface. The one or more sensor measurements are captured by a sensor disposed at a first end of a sensor probe, the first end being configured to extend beneath the skin surface to contact the interstitial fluid, and the sensor probe having a second end attached to the flexible substrate. The NFC transmitter receives the measurements made by the sensor and provides information indicative of the measurements to the controller. The controller receives the information when the controller is within a predetermined range from the NFC transmitter. The predetermined range is suitable for NFC.

At block 604, the method 600 includes determining a glucose concentration based on the information. In an example, the controller may be configured to process the sensor measurements to determine glucose concentration in the interstitial fluid. Glucose concentration in the interstitial fluid is indicative of glucose concentration in the blood stream. As an example, the controller may have access to a predetermined (e.g., empirical) relationship between the glucose concentration in the interstitial fluid and the corresponding blood glucose concentration. The controller may use such relationship to determine a blood glucose concentration for a patient based on the glucose concentration in the interstitial.

At block 606, the method 600 includes obtaining a target glucose concentration. As described above with respect to FIG. 5, the controller may be in communication with the set-point module and/or the patient-specific information module. The controller may be configured to receive from either module a target glucose concentration or a target range of glucose concentration (blood or interstitial fluid) to be maintained in the patient and is considered healthy for the patient.

In some examples, the controller may be configured to determine the target or the target range based on information provided by the set-point module and/or the patient-specific information module. In examples, the target and/or the target range may be dynamic, i.e., changes over time based on other factors such as other health conditions or indicators in the blood or interstitial fluid of the patient, time of day, meals consumed, or any other factor. In other examples, the target and/or the range may be fixed.

At block 608, the method 600 includes comparing the glucose concentration to the target glucose concentration. The controller may be configured to compare the target and/or target glucose concentration with a current glucose concentration in the blood of the patient determined at block 604. Accordingly, the controller may be configured to determine an error or discrepancy between the target and/or target range of glucose concentration and the current glucose concentration.

At block 610, the method 600 includes, based on the comparing, providing instructions to an insulin delivery device to control an insulin delivery rate to a blood stream by the insulin delivery device. Based on the discrepancy or error between the target and/or target range of glucose concentration and the current glucose concentration, the controller may be configured to provide instructions or commands (e.g., the commands described at FIG. 5) to control an insulin delivery device (e.g., an insulin pump).

In an example, in addition to the comparing, the controller may take into consideration diet and exercise information associated with the patient in to determine a proper insulin amount or insulin delivery rate appropriate for the patient. The diet and exercise information may be provided to the controller by, for example, the patient-specific information module 510 discussed with respect to FIG. 5, for example. The insulin delivery device can be mounted to an arm of the patient or any other place (e.g., on a belt worn by the user) and is configured to inject insulin at a particular rate or dosage into a blood stream of the patient.

In an example, the controller may provide the instructions such that the insulin delivery device provides insulin at a rate that would cause the blood glucose concentration of the patient to substantially meet the target glucose concentration. The blood glucose concentration substantially meets the target glucose concentration when the blood glucose concentration is within a predetermined threshold value from the target glucose concentration (e.g., within 2% from the target glucose concentration). For example, the insulin delivery device may be configured, based on the instructions from the controller, to adjust (e.g., increase, decrease, or maintain) the insulin delivery rate so as to cause the blood glucose concentration of the patient to substantially meet the target glucose concentration.

In another example, the controller may establish, based on the sensor measurements, a target rate of change of glucose concentration that enables changing the glucose concentration and reaching a target concentration within a predetermined period of time. The controller may then control the insulin delivery device pump to adjust the delivery rate to achieve the target rate of change.

In another example, the controller may establish a range of glucose concentration about the target glucose concentration based on the patient-specific information. The controller may then provide instructions to the insulin delivery device to maintain a predetermined insulin delivery rate by the insulin delivery device when the glucose concentration is within a target range. If the glucose concentration deviates from the range, the controller may be configured to provide instructions such that the insulin delivery device changes the insulin delivery rate to the blood stream so as to bring the glucose concentration in the blood stream within the range.

In examples, the controller may be embedded within a display device such as a wearable, laptop, desktop, handheld, or tablet computer, a mobile phone, a head-mounted display, or a subsystem of such a device. The display device may include a user interface. The user interface may include a data input device and/or a data output device.

In examples, the controller may generate signals or alerts that are then displayed on the data output device. For example, if the NFC transmitter has been out of communication range with the controller for a particular period of time, the controller may generate an alert to indicate to the user that the controller should be brought within NFC range from the NFC transmitter. As another example, if the glucose concentration level is dangerous to the patient, the controller may generate an alert that the patient should go to the hospital. The display device may also show status of the controller and/or other patient's vital indicators.

The data input device may include dials, buttons, pointing devices, manual switches, alphanumeric keys, a touch-sensitive display, combinations thereof, and/or the like for receiving patient and/or operator inputs. The data input device may be used for scheduling and/or initiating insulin bolus injections for meals, inputting patient-specific information, etc. Other input and output device are possible as well.

VI. CONCLUSION

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. It is also to be understood that the terminology used herein is for the purpose of describing particular implementations only, and is not intended to be limiting.

What is claimed is:

1. A system comprising:
   a flexible substrate;
   a sensor probe having a first end and a second end configured to contact interstitial fluid, wherein the second end is configured to measure a physiological property related to glucose in the interstitial fluid;
   a controller electrically coupled to the sensor probe via the first end; and
   a near field communication (NFC) device mounted to the flexible substrate and electrically coupled to the sensor probe, wherein the NFC device is configured to receive, from the sensor probe, one or more sensor measurements indicative of the physiological property, and wherein the NFC device is configured to detect the controller and provide information related to the one or more sensor measurements to the controller when the controller is detected,
   wherein the controller is configured to: (i) receive the information related to the one or more sensor measurements from the NFC device, (ii) determine a glucose concentration based on the information, (iii) obtain a target glucose concentration, (iv) compare the glucose concentration to the target glucose concentration, and (v) based on comparing the glucose concentration to the target glucose concentration, provide instructions to control an insulin delivery rate to a blood stream by an insulin delivery device.

2. The system of claim 1, further comprising an adhesive layer disposed on the flexible substrate, wherein the adhesive layer is configured to adhere the flexible substrate to a skin surface.

3. The system of claim 1, wherein the flexible substrate comprises polyimide.

4. The system of claim 1, wherein the NFC device includes an antenna disposed on the flexible substrate, wherein the NFC device is configured to communicate the information related to the one or more sensor measurements to the controller by way of the antenna.

5. The system of claim 1, wherein the NFC device is configured to periodically communicate the information related to the one or more sensor measurements to the controller without receiving commands from the controller.

6. The system of claim 1, wherein the controller is further configured to provide an alert after a particular period of time lapses without receiving the information from the NFC device.

7. The system of claim 1, wherein the sensor probe comprises two electrodes and is configured to measure the physiological property electrochemically.

8. The system of claim 1, wherein the controller is integrated into the insulin delivery device, the system further comprising:
   an NFC receiver coupled to the insulin delivery device and configured to receive the information related to the one or more sensor measurements from the NFC device and provide the information to the controller.

9. The system of claim 1, wherein the controller is configured to provide the instructions to a server that is in communication with the insulin delivery device.

10. A device comprising:
    a substrate;
    a sensor probe having a first end and a second end configured to contact interstitial fluid and measure a physiological property related to glucose in the interstitial fluid; and
    a near field communication (NFC) device mounted to the substrate and electrically coupled to the sensor probe, wherein the NFC device is configured to receive, from the sensor probe, one or more sensor measurements indicative of the physiological property, and wherein the NFC device is configured to detect a controller and provide information related to the one or more sensor measurements to the controller when the controller is detected so as to enable the controller to provide instructions to control an insulin delivery rate to a blood stream by an insulin delivery device.

11. The device of claim 10, further comprising an adhesive layer disposed on the substrate, wherein the adhesive layer is configured to adhere the substrate to a skin surface.

12. The device of claim 10, wherein the substrate comprises polyimide.

13. The device of claim 10, wherein the NFC device includes an antenna disposed on the substrate, wherein the NFC device is configured to communicate the information related to the one or more sensor measurements to the controller by way of the antenna.

14. The device of claim 10, wherein the NFC device is configured to periodically communicate the information related to the one or more sensor measurements to the controller without receiving commands from the controller.

15. The device of claim 10, wherein the sensor probe comprises two electrodes and is configured to measure the physiological property electrochemically.

16. A method comprising:
  receiving, at a controller from a close range wireless communication device, information indicative of one or more sensor measurements of a physiological property related to glucose in an interstitial fluid, wherein the close range wireless communication device comprises a near field communication (NFC) device, wherein the close range wireless communication device is mounted to a flexible substrate, wherein the one or more sensor measurements are captured by a first end of a sensor probe, the first end being configured to contact the interstitial fluid, wherein the sensor probe has a second end coupled to the flexible substrate, and wherein the close range wireless communication device is configured to detect the controller and provide the information indicative of the one or more sensor measurements to the controller when the controller is detected;
  determining a glucose concentration based on the information indicative of the one or more sensor measurements;
  obtaining a target glucose concentration;
  comparing the glucose concentration to the target glucose concentration; and
  based on the comparing, providing instructions to control an insulin delivery rate to a blood stream by an insulin delivery device.

17. The method of claim 16, further comprising:
  establishing a rate of change of glucose concentration based on the one or more sensor measurements, wherein providing the instructions is further based on an established rate of change of glucose concentration.

18. The method of claim 16, wherein the controller has access to patient-specific information, the method further comprising:
  establishing a range of glucose concentration about the target glucose concentration based on the patient-specific information, wherein providing the instructions comprises:
    providing instructions for maintaining a predetermined insulin delivery rate by the insulin delivery device when the glucose concentration is within the range of glucose concentration; and
    providing instructions for changing the insulin delivery rate by the insulin delivery device when the glucose concentration is outside of the range of glucose concentration.

19. The method of claim 16, providing instructions comprises:
  providing the instructions to a server in communication with the insulin delivery device.

20. The method of claim 16, wherein the controller is integrated into the insulin delivery device, and wherein receiving the information indicative of the one or more sensor measurements comprises:
  receiving the information from an close range wireless communication receiver coupled to the insulin delivery device and configured to receive the information from the close range wireless communication device.

* * * * *